US00PP22742P2

(12) United States Plant Patent
Dirr

(10) Patent No.: US PP22,742 P2
(45) Date of Patent: May 22, 2012

(54) ***PUNICA GRANATUM* PLANT NAMED 'ORANGE BLOSSOM SPECIAL'**

(50) Latin Name: ***Punica granatum* L.**
Varietal Denomination: Orange Blossom Special

(75) Inventor: Michael Dirr, Bogart, GA (US)

(73) Assignees: Plant Introductions Inc., Watkinsville, GA (US); University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 12/925,859

(22) Filed: Nov. 1, 2010

(51) Int. Cl.
*A01H 5/00* (2006.01)

(52) U.S. Cl. ..... Plt./210

(58) Field of Classification Search ..... Plt./210
See application file for complete search history.

(56) References Cited

OTHER PUBLICATIONS

Page from a booklet distributed to wholesale growers for Home Depot when they visited Plant Introductions nursery Jun. 16, 2010.*
Page 8 of Plant Introductions, Inc. booklet showing 'Orange Blossom Special' Jan. 2010.*
Plant Introductions Inc. poster showing new plants as displayed Feb. 17, 2010 at Pike Nurseries Employee Knowledge Fair.*
Page 8 of Plant Introductions, Inc. booklet showing 'Orange Blossom Special' as distributed to wholesale growers from Jan. 2010 on.
Plant Introductions, Inc. poster showing new plants (including *Punica Granatum* 'Orange Blossom Special') as displayed Feb. 17, 2010 at Pike Nurseries Employee Knowledge Fair.

* cited by examiner

*Primary Examiner* — Annette Para
(74) *Attorney, Agent, or Firm* — Greenlee Sullivan P.C.

(57) ABSTRACT

A new and distinct cultivar of *Punica granatum* plant named 'Orange Blossom Special', characterized by its compact, mounding growth habit, small, lustrous, medium green foliage that turns bright yellow in fall, reddish-orange flowers produced in abundance from spring to fall, greenish-tan to reddish-green fruits, and root/crown cold hardiness to USDA Hardiness Zone 7.

3 Drawing Sheets

Genus and species of plant claimed: *Punica granatum* L.
Variety denomination: 'Orange Blossom Special'.

BACKGROUND OF THE INVENTION

The present invention relates to a new and distinct cultivar of *Punica granatum,* a member of the Punicaceae family, hereinafter referred to by its cultivar name 'Orange Blossom Special'. This cultivar is grown primarily as an ornamental for landscape use and for use as a potted plant.

The cultivar originated from an open-pollination of *Punica granatum* 'Nana' (unpatented) in Watkinsville, Ga., and was selected from the progeny of this pollination by continued evaluation for growth habit and flowering and fruiting characteristics. The seeds were first sown in a greenhouse. After germination, the resulting plants were moved outside to an outdoor nursery where they were transplanted to larger containers and evaluated. 'Orange Blossom Special' was discovered as one of these seedlings in the outdoor nursery.

'Orange Blossom Special' has been asexually reproduced by softwood cuttings since 2007 in Watkinsville, Ga. The characteristics of 'Orange Blossom Special' have been stable and reproduced true-to-type in successive vegetative generations.

SUMMARY OF THE INVENTION

'Orange Blossom Special' has not been observed under all possible environmental conditions. The phenotype may vary somewhat with changes in light, temperature, soil and rainfall without, however, any variance in genotype.

The following traits have been observed and represent the characteristics of 'Orange Blossom Special'. In combination these characteristics distinguish 'Orange Blossom Special' from all other varieties in commerce known to the inventor. 1) Compact, mounding growth habit. 2) Small, lustrous, medium green foliage that turns bright yellow in fall. 3) Reddish-orange flowers produced in abundance from spring to fall. 4) Greenish-tan to reddish-green fruits. 5) Root/crown cold hardiness to USDA Hardiness Zone 7.

'Orange Blossom Special' is distinguished from its female parent 'Nana' by its vigor, growth habit, flower color, and quantity of flowers and fruit produced. 'Orange Blossom Special' has a more vigorous, mounding growth habit, whereas 'Nana' has a less vigorous rounded growth habit. 'Orange Blossom Special' has reddish-orange flowers, whereas 'Nana' has orange flowers. 'Orange Blossom Special' flowers and fruits more prolifically than 'Nana'. There are no other cultivars of *Punica granatum* with this combination of characteristics known to the inventor.

Plants of 'Orange Blossom Special' can be compared to plants of the cultivar 'PIIPG-I' (U.S. Plant Pat. No. 21,031), a sibling of 'Orange Blossom Special', which originated from the same open-pollination of *Punica granatum* 'Nana'. However, in side-by-side comparisons conducted in Watkinsville, Ga., plants of 'Orange Blossom Special' differed from plants of 'PIIPG-I' in the following characteristics: 1. Plants of 'Orange Blossom Special' had fruit that was greenish-tan to reddish-green in color, whereas plants of 'PIIPG-I' had fruit that was maroon-purple in color; 2. Plants of 'Orange Blossom Special' had a compact, mounding growth habit, whereas plants of 'PIIPG-I' had an overall larger compact, upright spreading growth habit; 3. Plants of 'Orange Blossom Special' were less cold hardy than plants of 'PIIPG-I' in container and in-ground evaluations at Watkinsville, Ga.

BRIEF DESCRIPTION OF THE DRAWINGS

The accompanying illustrations show characteristics of 'Orange Blossom Special' in photographs as true to color as is reasonably possible to make in illustrations of this nature. Colors in the photographs may differ slightly from the color values cited in the detailed botanical description which accurately describe the colors of the new *Punica*.

DETAILED DESCRIPTION

Figure 1:
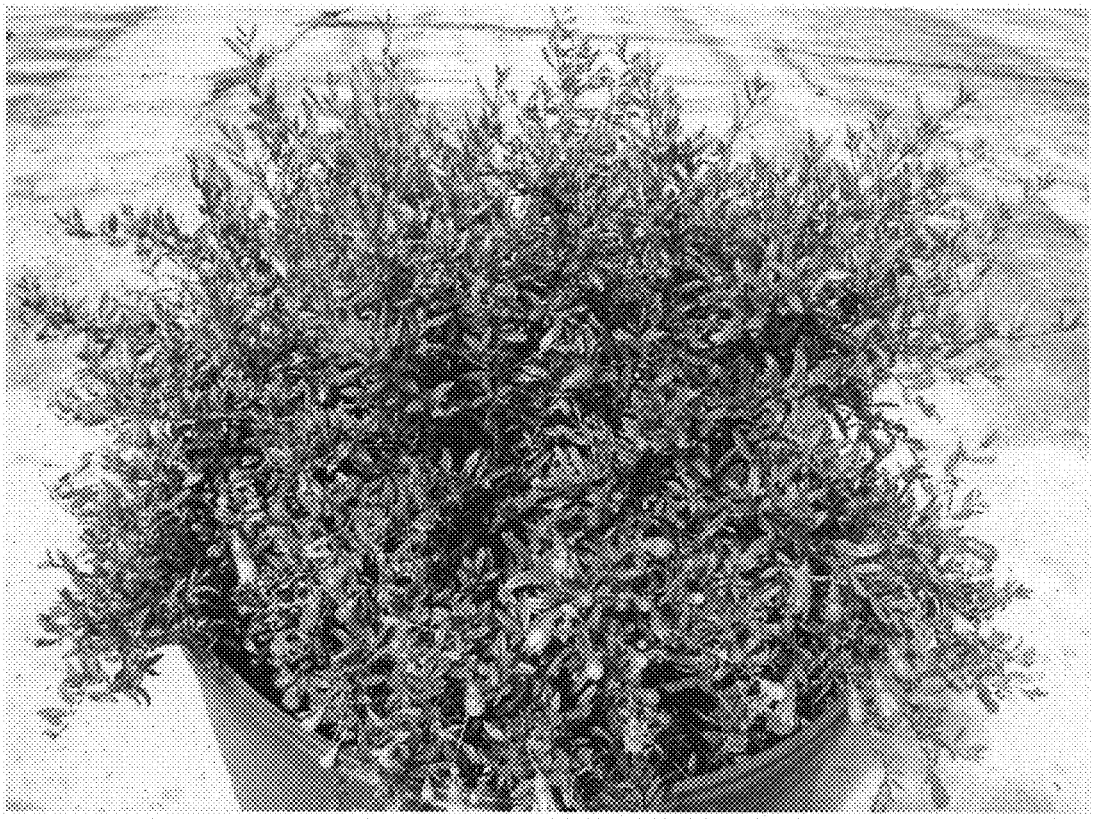
FIG. 1 shows the growth habit of 'Orange Blossom Special'.
Figure 2:
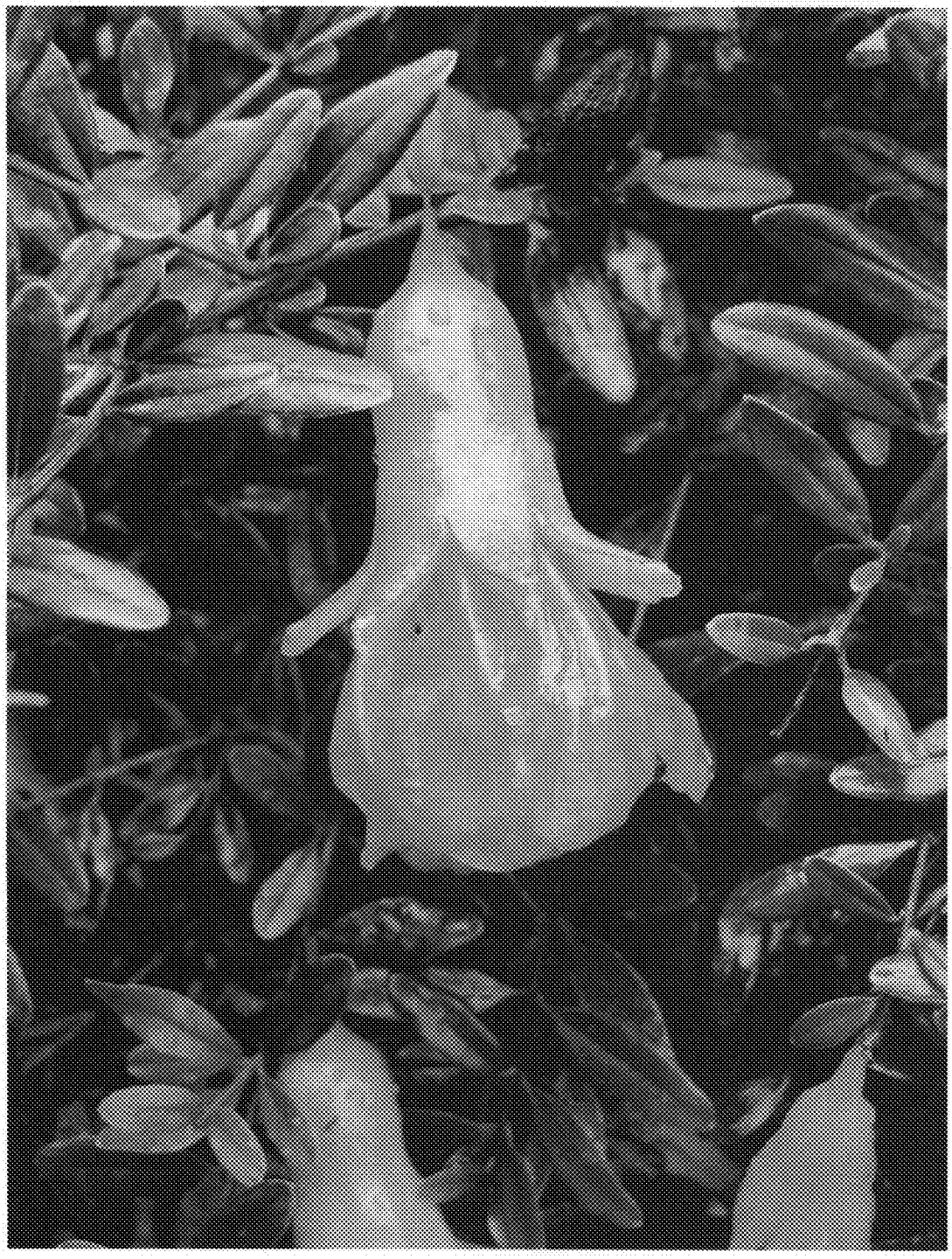
FIG. 2 shows a close-up of the flowers of 'Orange Blossom Special'.
Figure 3:
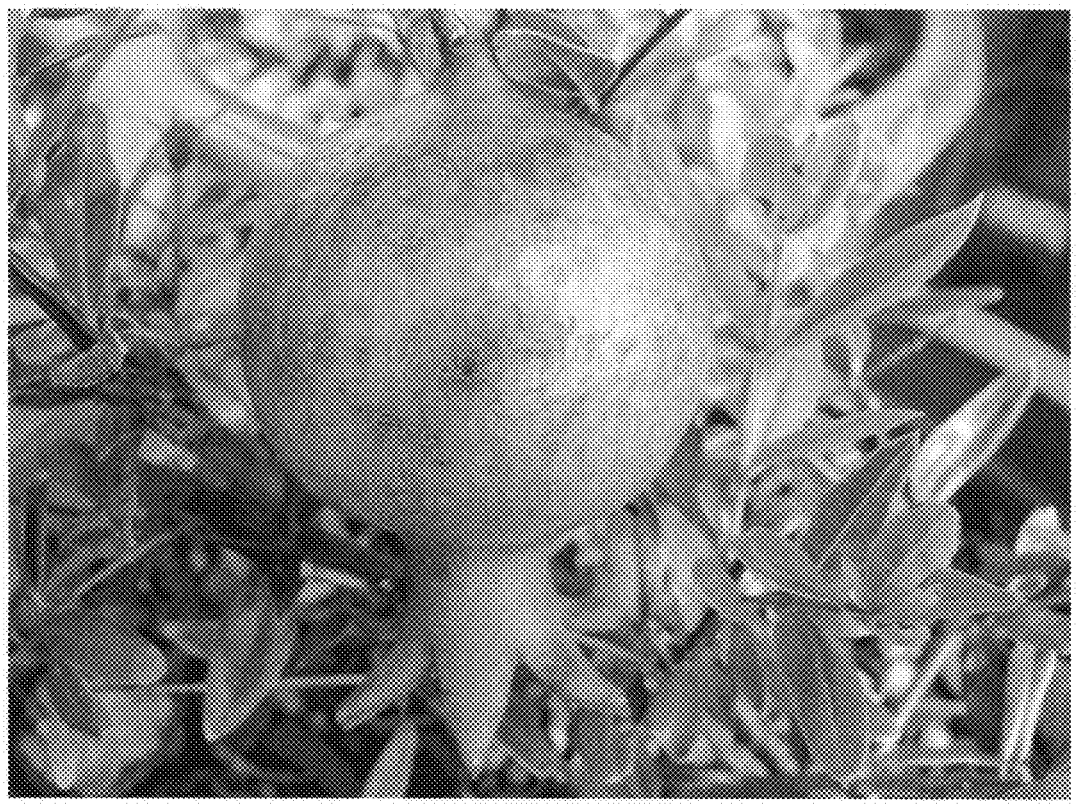
FIG. 3 shows a close-up of the fruits of 'Orange Blossom Special'.

In the following description, color references are made to The Royal Horticultural Society Colour Chart, 2001 Edition, except where general terms of ordinary dictionary significance are used. Plants used for the description were grown in 11.8 L containers in full sun under outdoor conditions in a nursery in Watkinsville, Ga. Plants were approximately 2½ years old when the description was recorded.

Botanical classification: 'Orange Blossom Special' is a cultivar of *Punica granatum*.

Parentage: The current variety is a progeny from an open-pollination of *Punica granatum* 'Nana'.

Propagation: Vegetatively by stem cuttings.

Plant description: The claimed variety is a freely branching, compact mounding deciduous shrub. The plant is root/crown hardy in USDA Zone 7 and stem hardy in USDA Zones 8 and 9.

*Root description.*—Numerous, fibrous, and well-branched.

*Plant height.*—About 45 cm from the soil to the top of the foliage.

*Plant diameter.*—About 55 cm.

Lateral branches having a length of about 10 to 15 cm.

*Stems.*—First year stems have a diameter of about 1.5 mm, an angled shape, and a glabrous texture. Pubescence: none. Exfoliation: on second year stems, stringy. The stem color is 53BA, maturing to N199A. Second year stems have a diameter of about 5 mm and the color is 197B. The main trunk is about 1.5 cm in diameter approximately 3 cm above the ground and the color is 197C.

Approximately 1 to 5 spines are present on most lateral branches. The spines range in length from about 1 to 4 cm and are about 1 mm in width. The color of the spines is 197B. The spines are somewhat flexible.

Lenticels are present on most stems and spines. Stems and spines have about 10 to 20 lenticels per cm of length. The round lenticels are about 1 mm in diameter and 199D in color.

*Internode length.*—About 7 mm.

*Vegetative buds.*—Arrangement: opposite to whorled. Shape: ovoid. Size: about 1 mm in length, about 1 mm in width; Color: 53A.

Foliage description:

*Arrangement.*—Opposite to whorled.

*Length.*—About 1.5 cm.

*Width.*—About 5 mm.

*Shape.*—Linear-lanceolate to linear.

*Apex.*—Obtuse.

*Base.*—Cuneate.

*Margin.*—Entire.

*Texture of upper and lower leaf surfaces.*—Glabrous, lustrous.

*Venation.*—Pinnate.

*Venation color on the upper and lower surfaces.*—144B.

*Color of emerging leaves.*—178C on the upper and lower surfaces.

*Color of young leaves.*—On the upper surface is 143A, and 144A on the lower surface.

*Color of mature leaves.*—On the upper surface is 137C, and 146A on the lower surface.

*Fall color.*—13B on upper and lower surfaces.

*Petiole length.*—About 1.5 mm.

*Petiole diameter.*—About 1 mm.

*Petiole texture.*—Glabrous.

*Petiole color.*—53B on upper and lower surfaces.

Flower description:

*Flower type and habit.*—Flowers are borne singly at the terminals. Individual flowers have 5 to 7 (typically 6) petals and the calyx has 5 to 7 (typically 6) lobes. Calyx has a funnel-shaped base and flowers appear similar to carnations. The calyx lobes (sepals) are about 7 mm in length and 5 mm in width, have an acute apex, a base that is fused to the calyx, lustrous texture on the upper and lower surfaces, and the color is 34A on the upper and lower surfaces. Individual flowers are showy for about 1 week.

*Bloom period.*—Spring to fall.

*Fragrance.*—None.

*Flower diameter.*—About 2 cm.

*Flower length.*—About 4 cm.

*Flower bud diameter.*—About 9 mm.

*Flower bud length.*—About 2.5 cm.

*Flower bud shape.*—Oblong.

*Flower bud color.*—N34B.

*Pedicels.*—About 2 mm in length, glabrous, and 187B in color.

Petals:

*Quantity.*—5 to 7 (typically 6) petals per flower.

*Petal length.*—1.9 cm.

*Petal width.*—1.5 cm.

*Petal shape.*—Spatulate with entire margin.

*Petal texture.*—Crumpled.

*Apex.*—Broad, rounded.

*Base.*—Cuneate to acute.

*Petal color.*—At peak bloom the upper and lower surfaces are 33A.

Stamens:

*Quantity.*—75 to 100 per flower.

*Anther diameter.*—About 1 mm.

*Anther color.*—8B.

*Filament length.*—About 1 cm.

*Filament diameter.*—About 0.5 mm in width.

*Filament color.*—33C. Pollen is produced in moderate quantities and the color is 8B.

Pistils:

*Quantity/arrangement.*—One per flower, inferior.

*Pistil length.*—About 1.5 cm.

*Pistil diameter.*—About 8 mm.

*Pistil color.*—8C.

*Stigma quantity/shape.*—1 per pistil, roughly diamond shaped, and about 1 mm in width.

*Stigma color.*—145B.

*Style shape and length.*—Tubular, about 1.2 cm.

*Style color.*—33C.

Fruit:

*Type/appearance.*—Berry, globose in shape with the persistent calyx at the apical end.

*Fruit length.*—About 4.5 cm.

*Fruit diameter.*—About 3.6 cm. Fruit stem length is about 2 mm and caliper is about 1 mm and color is 187B.

*Color of developing fruit.*—The main body color is 144B, overlaid with 178C and with blotches of N186C.

*Color of mature fruit.*—The main body color is 144A overlaid with 178B and with blotches of N186C. The surface or skin of the fruit is lustrous, leathery, and has round lenticels about 1 mm in diameter and 199D in color. The fruit, which are typically left on the plant for ornamental appeal, have a tendency to crack late in the season (mid to late fall).

*Quantity.*—The number of fruit per plant varies widely depending on the size and maturity of the plant. This cultivar is primarily grown as an ornamental and is not intended to be edible. Since this is a dwarf cultivar, the fruit remain small and bitter.

*Seeds.*—About 5 mm in length, about 3 mm in width, 199D in color, and each berry contains approximately 50 to 100 seeds.

Disease/pest resistance: No specific pest or disease resistance or susceptibility has been observed.

I claim:

1. A new and distinct *Punica granatum* plant named 'Orange Blossom Special', substantially as illustrated and described herein.

* * * * *